United States Patent [19]

Bruckner et al.

[11] Patent Number: 4,847,304

[45] Date of Patent: Jul. 11, 1989

[54] DISINFECTING AND STERILIZING COMPOSITION

[75] Inventors: Norman I. Bruckner, Plano; Michael D. Gordon; Ronald G. Howell, both of Arlington, all of Tex.

[73] Assignee: Surgikos, Inc., Arlington, Tex.

[21] Appl. No.: 53,210

[22] Filed: May 21, 1987

[51] Int. Cl.$^4$ ............................................. A61K 31/11
[52] U.S. Cl. ................................................... 514/699
[58] Field of Search ............... 514/705, 697, 698, 702, 514/699

[56] References Cited

U.S. PATENT DOCUMENTS

| | | | |
|---|---|---|---|
| 3,016,328 | 1/1962 | Pepper et al. | 514/702 |
| 3,282,775 | 11/1966 | Stonehill | 424/263 |
| 3,708,263 | 1/1973 | Boucher | 21/54 A |
| 3,912,450 | 10/1975 | Boucher | 21/54 A |
| 3,968,248 | 7/1976 | Boucher | 424/333 |
| 3,968,250 | 7/1976 | Boucher | 424/333 |
| 3,983,252 | 9/1976 | Buchalter | 424/333 |
| 4,436,754 | 3/1984 | Jacobs | 424/333 |

OTHER PUBLICATIONS

Rein et al., *Zentralblatt fuer Bakteralogie, Parasitenkunde, infektionskrankheitec und Hygeine,* 1 Abt. Orig B 172, pp. 508–519 (1981).

Rehn & Nolte, *Zentralblatt fuer Bakteralogie, Parasitenkunde, Infektionskrankheitec und Hygiene,* 1 Abt. Orig. B168, pp. 507–516 (1979), B172, pp. 508–519 (1981).

*Primary Examiner*—Douglas W. Robinson
*Assistant Examiner*—Richard Kearse
*Attorney, Agent, or Firm*—Michael Q. Tatlow; Charles J. Metz

[57] ABSTRACT

A sterilizing and disinfecting solution is disclosed. The solution contains a saturated dialdehyde such as glutaraldehyde and an aromatic dialdehyde, such as phthalaldehyde, isophthalaldehyde or terephthalaldehyde.

8 Claims, 1 Drawing Sheet

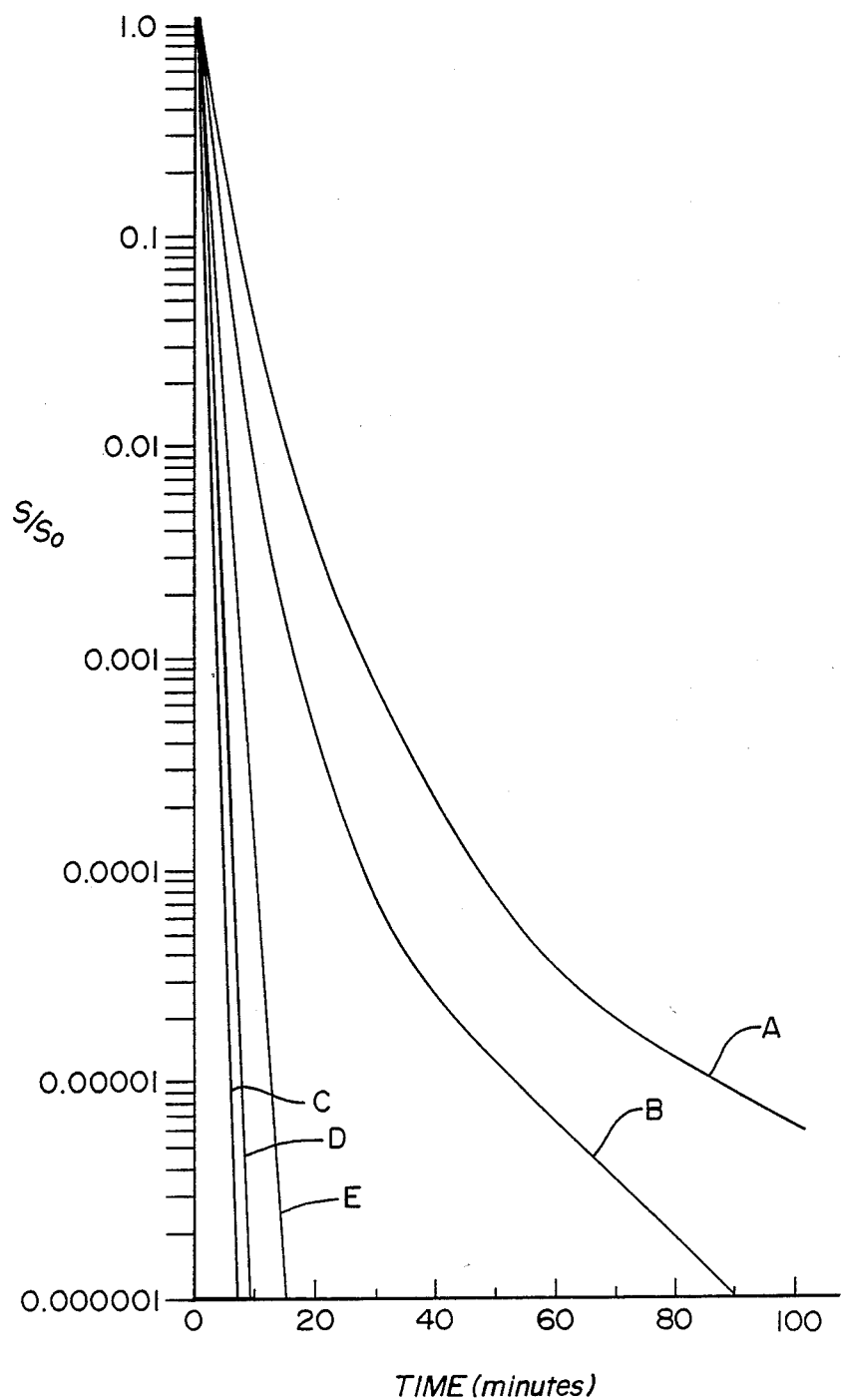

DISINFECTING AND STERILIZING COMPOSITION

FIELD OF INVENTION

This invention relates to improved sterilizing and disinfecting compositions which contain a saturated dialdehyde having from 2 to 6 carbon atoms and a water soluble aromatic dialdehyde. The aromatic dialdehydes include the three isomeric benzenedicarboxaldehydes: phthaladehyde, isophthalaldehyde and terephthalaldehyde. The present composition is particularly effective against *Mycobacterium tuberculosis* and closely related species at 20° C.

PRIOR ART

Saturated dialdehyde sterilizing and disinfecting compositions are well known. Pepper et al., U.S. Pat. No. 3,016,328; Stonehill, U.S. Pat. No. 3,282,775; Boucher, U.S. Pat. Nos. 3,708,263, 3,912,450, 3,968,248 and 3,968,250; and Buchalter, U.S. Pat. No. 3,983,252 all disclose the use of glutaraldehyde in aqueous or alcoholic solutions used to disinfect or sterilize medical devices or environmental surfaces.

Winicov, U.S. Pat. Nos. 4,048,336 and 4,093,744 teach sporicidal solutions which contain glutaraldehyde and a saturated monaldehyde. Formaldehyde, acetaldehyde, propionaldehyde and butyraldehyde are specifically identified as useful monoaldehydes.

Jacobs, U.S. Pat. No. 4,436,754 also disclosed sterilizing and disinfecting solutions which contain glutaraldehyde and formaldehyde.

Rehn and Nolte in *Zentralblatt fuer Bakteralogie, Parasitenkunde, Infektionskrankheitec und Hygiene.*, 1 Abt. Orig. B 168, pp. 507–516 (1979) disclose that a range of aromatic monoaldehydes and one aromatic dialdehyde, terephthaldehyde, have bacteriostatic and fungistatic activity.

Rehn, Nolte, and Zerling in *Zentralblatt fuer Bakteralogie, Parasitenkunde, infektionskrankheitec und Hygiene*, 1 Abt. Orig. B 172, pp 508–519 (1981) disclose that phthalaldehyde, isophthalaldehyde and terephthalaldehyde all have bacteriostatic and fungistatic activity.

Commercially available glutaraldehyde compositions of the type disclosed in the above mentioned U.S. patents have long been considered to be effective against a broad range of microorganisms, including *Mycobacterium tuberculosis* in ten (10) minutes at a temperature of 20° C. The test employed to make the determination of effectiveness was the AOAC Tuberculocidal Test, as specified in *Official Methods of Analysis* of the Association of Official Analytical Chemists, 14th Edition, 1984, Sections 4.045–4.050. In this Test, the organism employed is *Mycobacterium bovis* BCG.

It is now apparent that the standard AOAC test method gives highly erratic and variable results. This test method can show that a disinfectant composition is effective against *Mycobacterium bovis* BCG in 10 minutes, when in fact it is much less effective than the test indicated. An improved test method, which is both reproducible and quantitative, has been developed. The new test method uses the same test organism as the above mentioned AOAC Tuberculocidal Test. In this new test method, nine milliliters (ml) of the germicide to be tested in placed in a tube, put into a water bath and allowed to come to the desired temperature. One ml of the test organism (*M. bovis* BCG) is added to the tube containing the germicide to be tested. At appropriate time intervals, aliquots of the germicide-cell suspension are removed and added directly to an equal volume of appropriate neutralizer and mixed thoroughly. Ten-fold dilutions of the neutralized sample are prepared with saline dilution blanks. One ml of the appropriate dilutions are collected on the surface of membrane filters having a pore size of 0.45 micrometers. The filters are then washed with at least 50 ml of saline. The filters are placed on agar plates and incubated in plastic bags for 15 to 20 days at 37° C. The surviving colonies are then counted. Survival curves are constructed to determine the tuberculocidal activity of the solution. The data is plotted as $S/S_o$ vs. time. $S_o$ is the initial viable count of the test organism culture and S is the viable count at each time point.

When commercial glutaraldehyde solutions are tested using the new quantitative test method, these compositions do not kill the required $1 \times 10^5$ *Mycobacterium bovis* BCG in 10 minutes at 20° C. The additional exposure time required for complete kill at 20° may be as much as several hours. This exposure time becomes impractical, since the desired turn-around time for disinfection of equipment in the hospital is 30 minutes or less. In order to kill in 30 minutes a temperature of 25° C. is required, and in order to kill in 10 minutes a temperature of 30° C. is required.

Since the normal hospital room temperatures are between 20° C. and 25° C., additional costs associated with heating conventional glutaraldehyde compositions would be required to kill all the organisms within the desired 10 to 30 minute time frame.

SUMMARY OF THE INVENTION

It has now been discovered that the addition of relatively small amounts of an aromatic dialdehyde to the saturated dialdehyde composition provides a sterilizing and disinfecting solution which gives much more rapid kill of *Mycobacterium bovis* BCG at 20° C. The addition of the aromatic dialdehyde does not diminish the capability of the composition to destroy other microorganisms including the very resistant bacterial spores.

BRIEF DESCRIPTION OF THE DRAWING

FIG. 1 is a semi-log graph plotting the ratio of the number of surviving organisms over the number of original organisms versus time for various germicidal solutions at 20° C.

DESCRIPTION OF THE INVENTION

The aromatic dialdehydes, which are useful in the present invention have the formula:

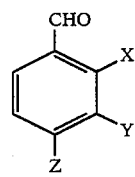

and are commonly called:
  phthalaldehyde, where X is CHO and Y and Z are H,
  isophthalaldehyde, where Y is CHO and X and Z are H, and
  terephthalaldehyde, where Z is CHO and X and Y are H.

The preferred aromatic dialdehyde is phthalaldehyde because of its good solubility in water and tuberculocidal activity.

The compositions of the present invention contain a saturated dialdehyde having 2 to 6 carbon atoms as the major antimicrobial in the compositions. The saturated dialdehydes which are known to have sporicidal activity are malonaldehyde, succinaldehyde, glutaraldehyde, adipaldehyde, and oxalaldehyde. The preferred saturated dialdehyde is glutaraldehyde.

The concentration of glutaraldehyde in the composition is generally between 0.25 and 6% by weight at the dilution or concentration when the composition is used. Higher concentrations of glutaraldehyde, i.e., 10–30% may be used for shipping the composition to the point of use and the composition would then be diluted to the desired use concentration.. The preferred concentration of glutaraldehyde at use is between 1% and 4%.

The aromatic dialdehyde is present in the composition, at use concentration, in amount of between 0.005% and 1% by weight based on the total weight of the composition. The preferred concentration being from 0.01% to 0.3% on the same basis. The limits on the amount of the aromatic dialdehyde used in the present composition is a function of the solubility of the particular aromatic dialdehyde in water. It is possible to increase the concentration of a particular aromatic dialdehyde in the solution by dissolving the aromatic dialdehyde in a co-solvent, miscible with water, and adding the dissolved aromatic dialdehyde to water. Suitable co-solvents include methanol, ethanol, isopropanol, polyols, tetrahydrofuran, dimethylsulfoxide and dioxane.

An alkalinating salt is used in the composition as a buffer to maintain the proper pH of the composition during use. The alkalinating salt may be the type disclosed in the Pepper et al., U.S. Pat. No. 3,016,328, which is an alkali metal carbonate or bicarbonate, e.g., sodium bicarbonate or potassium bicarbonate, or may be a phosphate. The buffer may also be an organic carboxylate salt such as sodium citrate, sodium acetate, potassium citrate or potassium acetate. The particular salt or mixtures of salt are present in a sufficient amount, 0.1% to 2.5% based on the total weight of the solution, to give the desired pH. The pH of the composition, to obtain the optimum antimicrobial activity at room temperature, is between pH 7.0 and 9.0. However, the tuberculocidal activity enhancement provided by the aromatic dialdehyde is not dependent on pH.

The composition may contain other ingredients such as a surfactant, an odor suppressant, a corrosion inhibitor, a stabilizer for the saturated dialdehyde to inhibit polymerization, an antioxidant, sequesterent, a dye and a fragrance. The use of these other ingredients is well-known in the art.

The compositions of the present invention may be formulated in two or more parts which are combined immediately prior to use. The formulation of the composition into multiple parts extends the shelf life of the composition. The saturated dialdehydes are more effective against bacterial spores at an alkaline pH. However, the saturated dialdehydes also have a tendency to polymerize with themselves or with the aromatic dialdehyde at an alkaline pH, thereby reducing the effective concentration of both the dialdehydes in the composition. The dialdehydes of the present invention can be formulated in an aqueous solution at an acid pH, and activated with an alkalinating agent immediately prior to use, shifting the pH to the alkaline range. This procedure is disclosed in the previously mentioned Pepper et al., U.S. Pat. No. 3,016,328.

In the following Examples, all percentages are weight percentages, based on the total weight of the solutions unless otherwise indicated. The bacteriological testing was by the new tuberculocidal test methodology previously described.

EXAMPLE I

In the Example, small amounts of phthalaldehyde, isophthalaldehyde and terephthalaldehyde were added to 2% glutaraldehyde solutions and tested to show the effectiveness of the compositions in killing *Mycobacterium bovis* BCG at 20° C. The amount of isophthalaldehyde or terephthalaldehyde added was based on their solubility limit in water. The test solutions were all buffered with 0.6% dipotassium hydrogen phosphate, and the pH of the solutions was adjusted to 8 with 1N $H_3PO_4$. The results of these tests are shown in Table I.

TABLE I

| Aromatic Dialdehyde | % Aromatic Dialdehyde (w/w) | Number of Organisms Surviving | | |
|---|---|---|---|---|
| | | 0 min | 10 min | 20 min |
| None | | $3.8 \times 10^5$ | $1.3 \times 10^4$ | $1.2 \times 10^3$ |
| Phthalaldehyde | 0.10 | $2.4 \times 10^5$ | 0 | 0 |
| Isophthalaldehyde | 0.25 | $3.8 \times 10^5$ | 0 | 0 |
| Terephthalaldehyde | 0.10 | $3.8 \times 10^5$ | $2.0 \times 10^1$ | 0 |

The results indicate that the aromatic dialdehydes shown in Table I provide excellent tuberculocidal activity enhancement at 20° C.

EXAMPLE II

In the Example, the aromatic dialdehydes were tested in aqueous solution containing no glutaraldehyde to determine the effect of the same low concentrations of aromatic dialdehydes, as in Example I, against the same organism at 20°. The solutions were buffered and the pH was adjusted to 8.0 as in Example I. The results are shown in Table II.

TABLE II

| Aromatic Dialdehyde | % Aromatic Dialdehyde (w/w) | Number of Organisms Surviving | | |
|---|---|---|---|---|
| | | 0 min. | 10 min. | 20 min. |
| Phthalaldehyde | 0.10 | $3.8 \times 10^5$ | 0 | 0 |
| Isophthalaldehyde | 0.25 | $2.8 \times 10^5$ | $2.3 \times 10^5$ | $2.3 \times 10^5$ |
| Terephthalaldehyde | 0.10 | $2.8 \times 10^5$ | $3.3 \times 10^5$ | $4.0 \times 10^5$ |

The results show that phthalaldehyde has excellent tuberculocidal activity by itself and isophthalaldehyde and terephthalaldehyde at their water solubility limit do not have any appreciable tuberculocidal activity by themselves. Use of 20% alcohol co-solvent only modestly increased the amount of isophthalaldehyde and terephthalaldehyde in the test solutions.

EXAMPLE III

A series of solutions containing 2% glutaraldehyde and various concentrations of phthalaldehyde were prepared. The solutions were buffered to pH 8 as in Example 1 and tested for their effectiveness in killing Mycobacterium bovis BCG at 20° C. The results are shown in Table III.

TABLE III

| % Phthal-aldehyde (w/w) | Number of Organisms Surviving | | | |
|---|---|---|---|---|
| | 0 min | 10 min | 20 min | 30 min |
| 0.10 | $2.4 \times 10^5$ | 0 | 0 | 0 |
| 0.05 | $2.4 \times 10^5$ | $2.0 \times 10^0$ | 0 | 0 |
| 0.025 | $2.4 \times 10^5$ | $4.0 \times 10^1$ | 0 | 0 |
| 0.01 | $2.4 \times 10^5$ | $9.4 \times 10^2$ | $6.0 \times 10^0$ | 0 |
| 0.005 | $2.4 \times 10^5$ | $2.1 \times 10^3$ | $1.3 \times 10^2$ | 0 |
| 0 | $2.4 \times 10^5$ | $3.5 \times 10^3$ | $1.0 \times 10^3$ | $1.1 \times 10^2$ |

The results show that compositions containing 2% glutaraldehyde and as low as 0.005% phthalaldehyde are tuberculocidal within 30 minutes at 20° C.

EXAMPLE IV

A series of solutions containing 0.75% or less of glutaraldehyde and 0.05% or less of phthaladehyde were prepared. The solutions were buffered to pH 8 as in Example I and tested for their effectiveness in killing Mycobacterium bovis BCG at 20° C. The results are shown in Table IV.

TABLE IV

| % Glutar-aldehyde (w/w) | % Phthal-aldehyde (w/w) | Number of Organisms Surviving | | | |
|---|---|---|---|---|---|
| | | 0 min | 10 min | 20 min | 30 min |
| 0.75 | 0.05 | $3.4 \times 10^5$ | 0 | 0 | 0 |
| 0.75 | 0.025 | $3.4 \times 10^5$ | $4.2 \times 10^1$ | 0 | 0 |
| 0.75 | 0.01 | $3.4 \times 10^5$ | $2.6 \times 10^3$ | $7.4 \times 10^1$ | 0 |
| 0.50 | 0.05 | $3.4 \times 10^5$ | 0 | 0 | 0 |
| 0.50 | 0.025 | $3.4 \times 10^5$ | $2.8 \times 10^1$ | 0 | 0 |
| 0.50 | 0.01 | $3.4 \times 10^5$ | $3.8 \times 10^3$ | $3.5 \times 10^2$ | $1.4 \times 10^1$ |
| 0.25 | 0.05 | $3.4 \times 10^5$ | $1.2 \times 10^2$ | 0 | 0 |
| 0.25 | 0.025 | $3.4 \times 10^5$ | $3.3 \times 10^2$ | 0 | 0 |
| 0.25 | 0.01 | $3.4 \times 10^5$ | $5.9 \times 10^3$ | $1.6 \times 10^3$ | $2.9 \times 10^2$ |

The results show that compositions containing 0.75% glutaraldehyde and only 0.01% phthalaldehyde or 0.25% glutaraldehyde and 0.025% phthalaldehyde are tuberculocidal within 30 minutes at 20° C.

EXAMPLE V

Portions of a solution containing 2% glutaraldehyde, 0.10% phthalaldehyde and 0.6% dipotassium hydrogen phosphate were adjusted to different pH levels with $H_3PO_4$ and KOH. The solutions were tested against Mycobacterium bovis BCG at 20° C. to determine the effect of pH on the effectiveness of the solutions. The results are shown in Table V.

TABLE V

| pH | Number of Organisms Surviving | | | |
|---|---|---|---|---|
| | 0 min | 10 min | 20 min | 30 min |
| 3 | $3.8 \times 10^5$ | 0 | 0 | 0 |
| 5 | $3.8 \times 10^5$ | 0 | — | — |
| 7 | $3.8 \times 10^5$ | 0 | 0 | — |
| 9 | $3.8 \times 10^5$ | 0 | 0 | — |

The results indicate that the tuberculocidal activity of compositions containing glutaraldehyde and phthalaldehyde is not pH dependent.

EXAMPLE VI

A solution containing 2.0% glutaraldehyde and 0.1% phthalaldehyde was tested against a 2.0% glutaraldehyde solutions to compare their effectiveness in killing spores of Bacillus subtilis and Clostridium sporogenes at 20° C. in 10 hours using the standard AOAC Method (AOAC Official Methods of Analysis, 14th edition, 1984, page 72). The solutions were buffered to pH 8 as in Example I. A surfactant (Pluronic P103, BASF Wyandotte, 0.2% w/w) was added to each solution to insure wetting of the silk suture and porcelain penicylinder tests carriers. The results are shown in Table VI.

TABLE VI

| % Glutar-aldehyde (w/w) | % Phthal-aldehyde (w/w) | Total No. of Positives (Failures/ Total No. of Tests) | | | |
|---|---|---|---|---|---|
| | | B. subtilis | | C. sporogenes | |
| | | sutures | peni-cylinders | sutures | peni-cylinders |
| 2.0 | 0 | 0/30 | 0/30 | 0/30 | 0/30 |
| 2.0 | 0.1 | 0/30 | 0/30 | 0/30 | 0/30 |

The results indicate that the addition of 0.1% phthalaldehyde does not inhibit the sporicidal activity of 2% glutaraldehyde.

FIG. 1 graphically illustrates the tuberculocidal enhancement provided by the addition of small amounts of an aromatic dialdehyde to glutaraldehyde solutions. The organisms tested was Mycobacterium bovis BCG. The curves shown in FIG. 1 are plots of $S/S_o$ versus time for the following solutions (all solutions were tested at 20 C. and at pH 8):

| Curve | Active Ingredients |
|---|---|
| A | 2% glutaraldehyde |
| B | 3% glutaraldehyde |
| C | 2% glutaraldehyde and 0.10% phthalaldehyde |
| D | 2% glutaraldehyde and 0.25% isophthalaldehyde |
| E | 2% glutaraldehyde and 0.10% terephthalaldehyde |

As indicated in FIG. 1, the presence of the aromatic dialdehydes in the solution, results in a significant reduction in the time required for total kill of the organism.

We claim:

1. A sterilizing and disinfecting solution with enhanced tuberculocidal activity containing from 0.25% to 6% by weight of glutaraldehyde and from 0.01% to 1% by weight of a water soluble aromatic dialdehyde selected from the group consisting of phthalaldehyde, isophthalaldehyde and terephthalaldehyde.

2. The composition of claim 1 in which the glutaraldehyde concentration is between 1 and 4% by weight.

3. The composition of claim 1 in which the aromatic dialdehyde is phthalaldehyde.

4. The composition of claim 1 in which the aromatic dialdehyde is isophthalaldehyde.

5. The composition of claim 1 in which the aromatic dialdehyde is terephthaldehyde.

6. The solution of claim 2 containing from 2 to 4% by weight glutaraldehyde.

7. The solution of claim 1 in which the pH of the solution is in the range of pH 3 to pH 9.

8. The solution of claim 2 in which the pH of the solution in the range of pH 7 to pH 9.

* * * * *